(12) United States Patent
Jeter et al.

(10) Patent No.: US 10,143,808 B2
(45) Date of Patent: Dec. 4, 2018

(54) CONTAINER FOR INJECTION DEVICE WITH INJECTION NEEDLE

(71) Applicant: BECTON, DICKINSON AND COMPANY, Fraklin Lakes, NJ (US)

(72) Inventors: Ruane S. Jeter, Wyckoff, NJ (US); Richard A. Cronenberg, Mahwah, NJ (US); Lionel Vedrine, Palo Alto, CA (US); Atul Patel, Wilkes-Barre, PA (US); Dnyanesh Talpade, Kinnelon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 546 days.

(21) Appl. No.: 14/280,769

(22) Filed: May 19, 2014

(65) Prior Publication Data
US 2014/0251847 A1 Sep. 11, 2014

Related U.S. Application Data

(63) Continuation of application No. 13/119,076, filed as application No. PCT/US2009/057424 on Sep. 18, 2009, now Pat. No. 8,728,028.
(Continued)

(51) Int. Cl.
*A61M 5/00* (2006.01)
*A61M 5/315* (2006.01)
(Continued)

(52) U.S. Cl.
CPC .......... *A61M 5/3158* (2013.01); *A61M 5/002* (2013.01); *A61M 5/3205* (2013.01);
(Continued)

(58) Field of Classification Search
CPC .. A61M 5/002; A61M 5/3205; A61M 5/3213; A61M 5/321; A61M 5/3158
(Continued)

(56) References Cited

U.S. PATENT DOCUMENTS

| | | | | |
|---|---|---|---|---|
| 3,746,155 A | * | 7/1973 | Seeley | B65D 75/368 206/229 |
| 3,869,062 A | * | 3/1975 | Jaeschke | B65D 5/5016 206/229 |

(Continued)

FOREIGN PATENT DOCUMENTS

| | | |
|---|---|---|
| EP | 1669097 A2 | 6/2006 |
| JP | 1-119646 | 8/1989 |

(Continued)

OTHER PUBLICATIONS

European Patent Office, Extended European Search Report, European Patent Application No. 09815241.6 (PCT/US2009/057424), dated Nov. 12, 2014, Munich, Germany.

*Primary Examiner* — Steven A. Reynolds
(74) *Attorney, Agent, or Firm* — Dickinson Wright PLLC

(57) ABSTRACT

With the subject invention, a container for an injection device with an injection needle is provided. The container includes a body having a compartment formed therein to accommodate the injection device in both a pre-use and a post-use condition. The body defines a first opening through which the injection device in its pre-use condition may be accessed, and the body defines a second opening into which the injection device may be directed in its post-use condition. A closure is provided for closing the first opening. The container also includes a retainer for retaining the injection device in the container in its post-use condition preventing access to the injection needle after the injection device has been used to administer an injection. Advantageously, the container of the subject invention provides not only a (Continued)

pre-use packaging for the injection device, but also a post-use sharps container for the injection device.

19 Claims, 6 Drawing Sheets

Related U.S. Application Data

(60) Provisional application No. 61/192,465, filed on Sep. 18, 2008.

(51) Int. Cl.
*A61M 5/32* (2006.01)
*A61M 5/24* (2006.01)

(52) U.S. Cl.
CPC ... *A61M 5/3213* (2013.01); *A61M 2005/2407* (2013.01); *A61M 2005/2496* (2013.01)

(58) Field of Classification Search
USPC .............. 206/365, 366, 364, 367, 370, 363; 604/110
See application file for complete search history.

(56) References Cited

U.S. PATENT DOCUMENTS

| | | | |
|---|---|---|---|
| 4,578,064 A | | 3/1986 | Sarnoff et al. |
| 4,972,950 A * | | 11/1990 | Shillington ......... A61M 5/3205 206/366 |
| 5,031,767 A | | 7/1991 | Bruno |
| 5,092,462 A * | | 3/1992 | Sagstetter ........... A61M 5/3205 206/366 |
| 5,152,394 A * | | 10/1992 | Hughes ................. A61M 5/002 206/366 |
| 5,161,681 A * | | 11/1992 | Kemp ................ A61M 5/3205 206/210 |
| 5,183,156 A * | | 2/1993 | Bruno ................. A61M 5/3205 206/365 |
| 5,273,161 A * | | 12/1993 | Sagstetter ........... A61M 5/3205 206/366 |
| 5,322,164 A * | | 6/1994 | Richardson ......... A61M 5/3205 206/365 |
| 5,402,887 A * | | 4/1995 | Shillington ......... A61M 5/3205 206/366 |
| 5,415,315 A * | | 5/1995 | Ramirez ............... B65F 1/1607 206/366 |
| 5,494,158 A | | 2/1996 | Erickson |
| 5,857,569 A * | | 1/1999 | Hoftman ............ A61M 5/3205 206/365 |
| 6,253,916 B1 * | | 7/2001 | Bickel ................. A61M 5/3205 206/366 |
| 6,599,272 B1 | | 7/2003 | Hjertman et al. |
| 6,637,587 B2 * | | 10/2003 | Britton ................ A61M 5/3278 206/210 |
| 6,691,867 B1 * | | 2/2004 | Bickel ................. A61M 5/3205 206/366 |
| 6,783,003 B2 | | 8/2004 | Simm et al. |
| 6,923,319 B1 * | | 8/2005 | Erickson ............... A61M 5/008 206/366 |
| 7,445,116 B2 * | | 11/2008 | Dansaert .............. A61B 50/362 206/366 |
| 8,728,028 B2 * | | 5/2014 | Jeter ..................... A61M 5/002 206/210 |
| 2001/0037087 A1 | | 11/2001 | Knauer |
| 2002/0100706 A1 * | | 8/2002 | Sherman ............ A61M 5/3205 206/370 |
| 2003/0038046 A1 * | | 2/2003 | Panek, Jr. ........... A61M 5/3205 206/366 |
| 2003/0132129 A1 * | | 7/2003 | Erickson ............. A61M 5/3205 206/366 |
| 2003/0183546 A1 * | | 10/2003 | Crawford ............ A61B 50/362 206/366 |
| 2005/0197650 A1 | | 9/2005 | Sugimoto et al. |
| 2005/0269227 A1 * | | 12/2005 | Erickson ............ A61M 5/3205 206/366 |
| 2008/0210890 A1 | | 9/2008 | Fago |
| 2010/0282628 A1 | | 11/2010 | Mowe et al. |

FOREIGN PATENT DOCUMENTS

| | | |
|---|---|---|
| JP | 1-138425 | 9/1989 |
| JP | 3035292 B1 | 2/2000 |
| JP | 2008043503 A | 2/2008 |
| WO | 9106328 | 5/1991 |
| WO | 2003/080467 A1 | 10/2003 |
| WO | WO-2004/098687 A1 | 11/2004 |
| WO | WO-2005/077441 A2 | 8/2005 |
| WO | 2006/119247 A1 | 11/2006 |

* cited by examiner

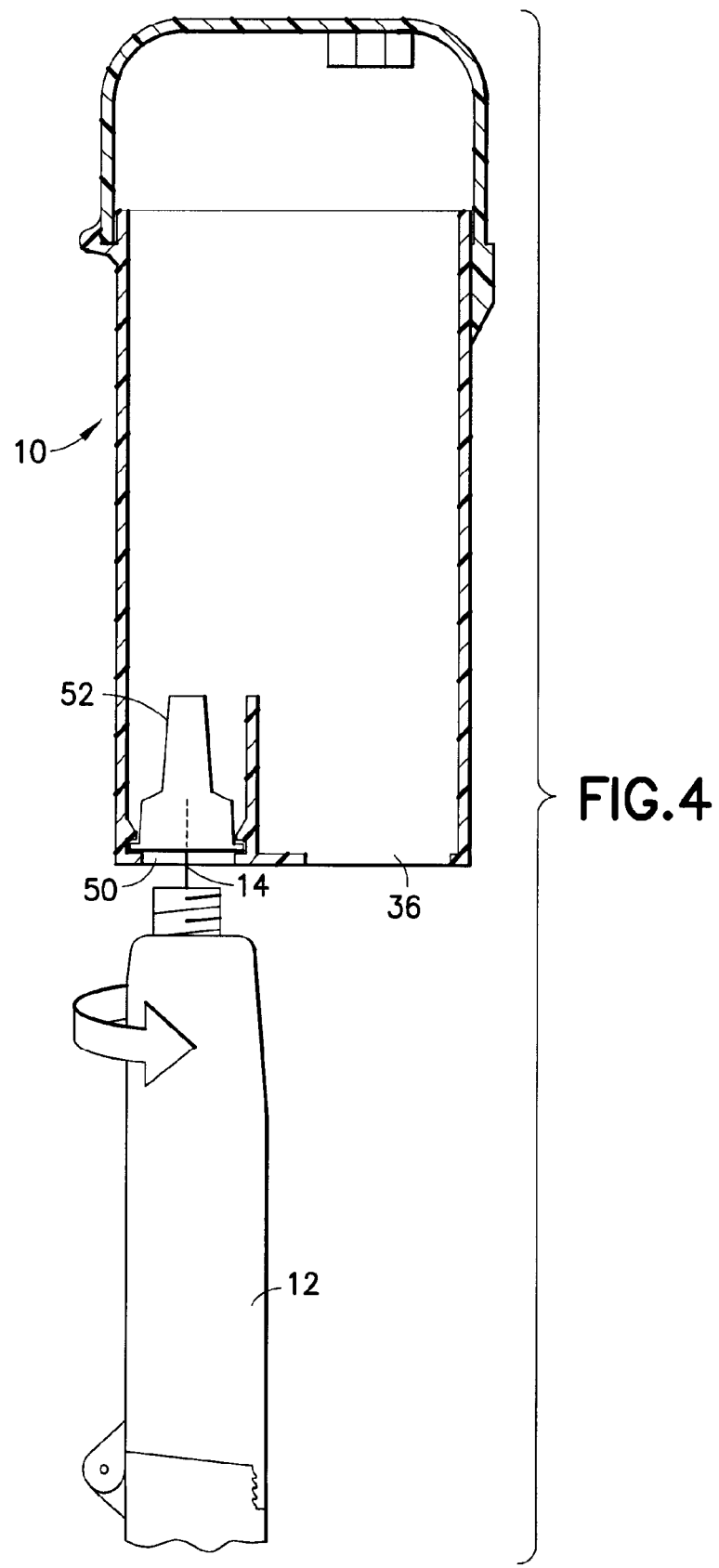

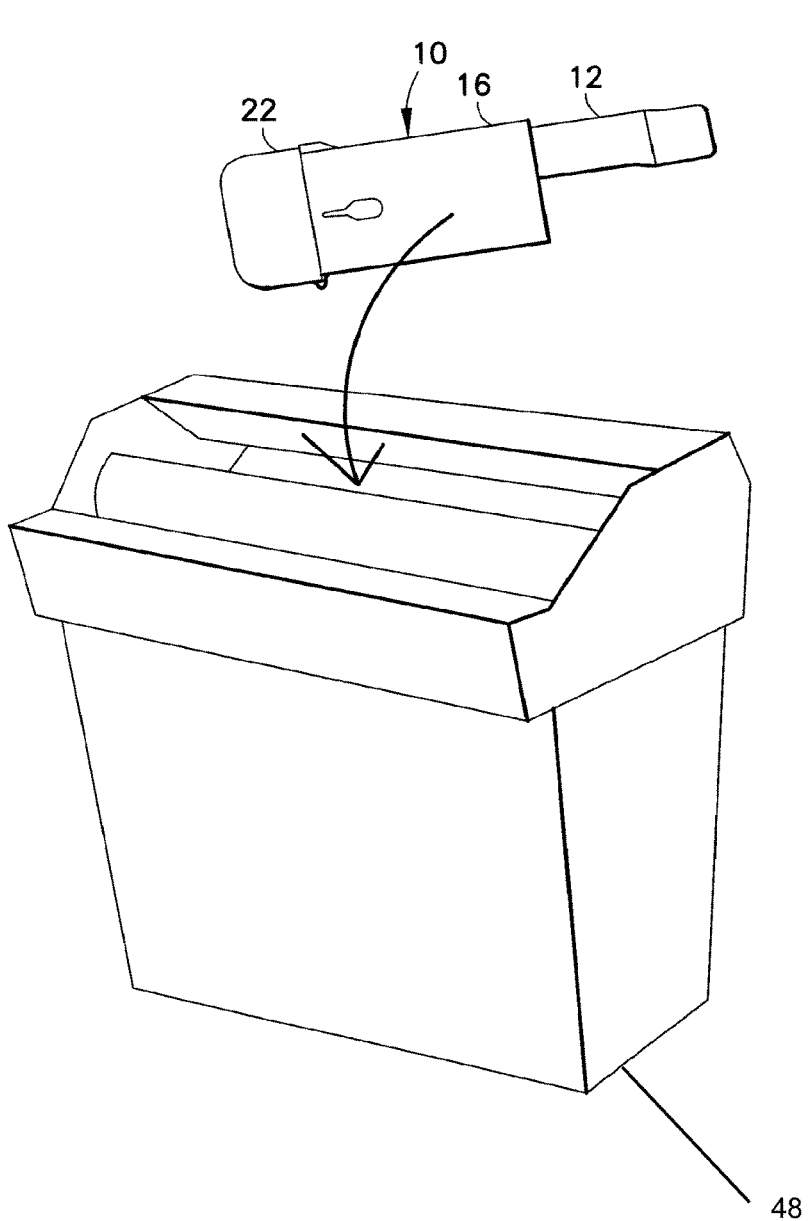

CONTAINER FOR INJECTION DEVICE WITH INJECTION NEEDLE

CROSS-REFERENCES TO RELATED APPLICATIONS

This application is a continuation of U.S. application Ser. No. 13/119,076, filed on Aug. 4, 2011, now U.S. Pat. No. 8,728,028, which is a National Stage Application under 35 U.S.C. § 371 of PCT/US2009/057424, filed on Sep. 18, 2009, which claims the benefit of priority to U.S. Provisional Application No. 61/192,465, filed on Sep. 18, 2008, the entire contents of these applications being incorporated by reference herein.

FIELD OF THE INVENTION

This invention relates to containers for injection devices with injection needles and, more particularly, to containers for accommodating injection devices before and after use.

BACKGROUND OF THE INVENTION

Concerns exist over "needle sticks" where a practitioner or other individual administering an injection is inadvertently stuck with a used medical needle. Needle sticks may result in a transmission of disease, such as AIDS or Hepatitis B. Various shields have been developed in the prior art to cover and limit access to a medical needle, particularly after use. In addition, a used needle is considered biohazardous waste and must be disposed of appropriately. Containers, commonly referred to as "sharps containers", are provided into which used needles, and other biohazardous materials, may be collected. Sharps containers typically have a waste-receptacle or mailbox-type design formed to receive and house spent devices.

SUMMARY OF THE INVENTION

With the subject invention, a container for an injection device with an injection needle is provided. The container includes a body having a compartment formed therein to accommodate the injection device in both a pre-use and a post-use condition. The body defines a first opening through which the injection device in its pre-use condition may be accessed, and the body defines a second opening into which the injection device may be directed in its post-use condition. A closure is provided for closing the first opening. The container also includes a retainer proximate the second opening for retaining the injection device in the container in its post-use condition preventing access to the injection needle after the injection device has been used to administer an injection. Advantageously, the container of the subject invention may accommodate an injection device both before and after use thereby providing not only a pre-use packaging for the injection device, but also a post-use sharps container for the injection device.

These and other features of the invention will be better understood through a study of the following detailed description and accompanying drawings.

BRIEF DESCRIPTION OF THE DRAWINGS

FIG. 4 is a schematic showing an injection needle being mounted onto an injection device utilizing a container formed in accordance with the subject invention;

DETAILED DESCRIPTION OF THE INVENTION

Figure 1:
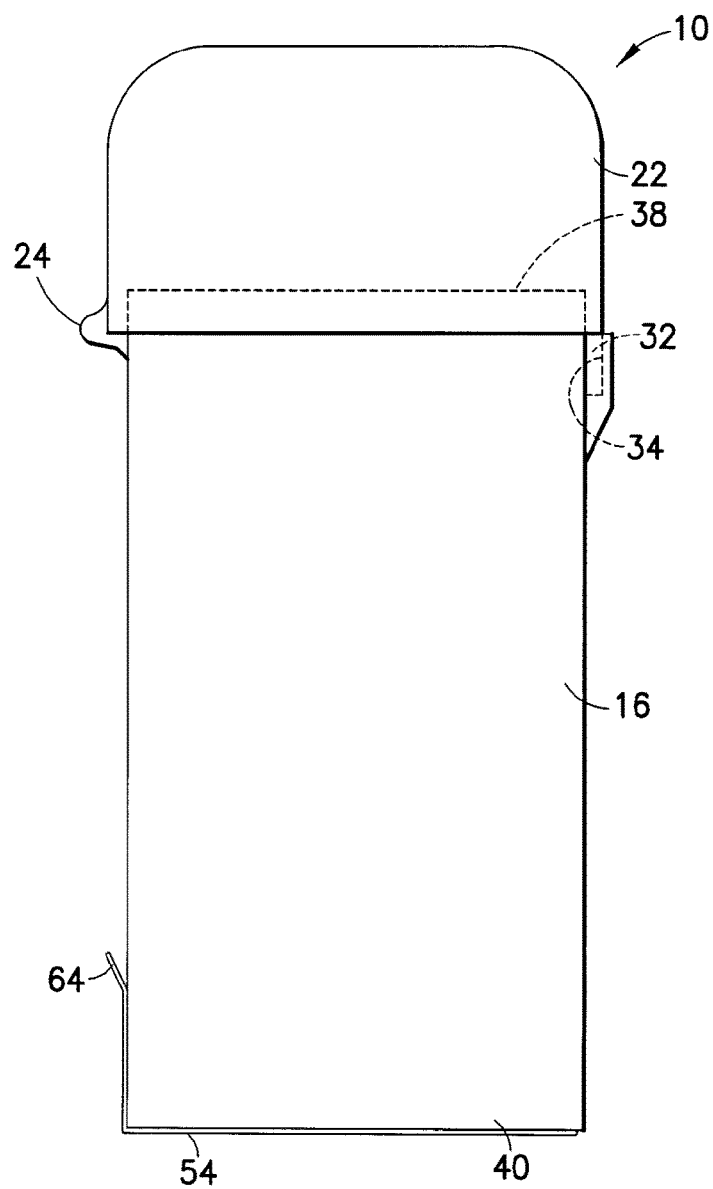
FIG. 1 is a front plan view of a container formed in accordance with the subject invention.

With reference to the figures, a container, generally designated with the reference numeral 10, is shown for accommodating an injection device 12 before and after use. The injection device 12 is a medical injection device, such as a syringe or pen injector, intended for injection of a medicament into a human or animal. An injection needle 14 is provided for use with the injection device 12.

Figure 2:
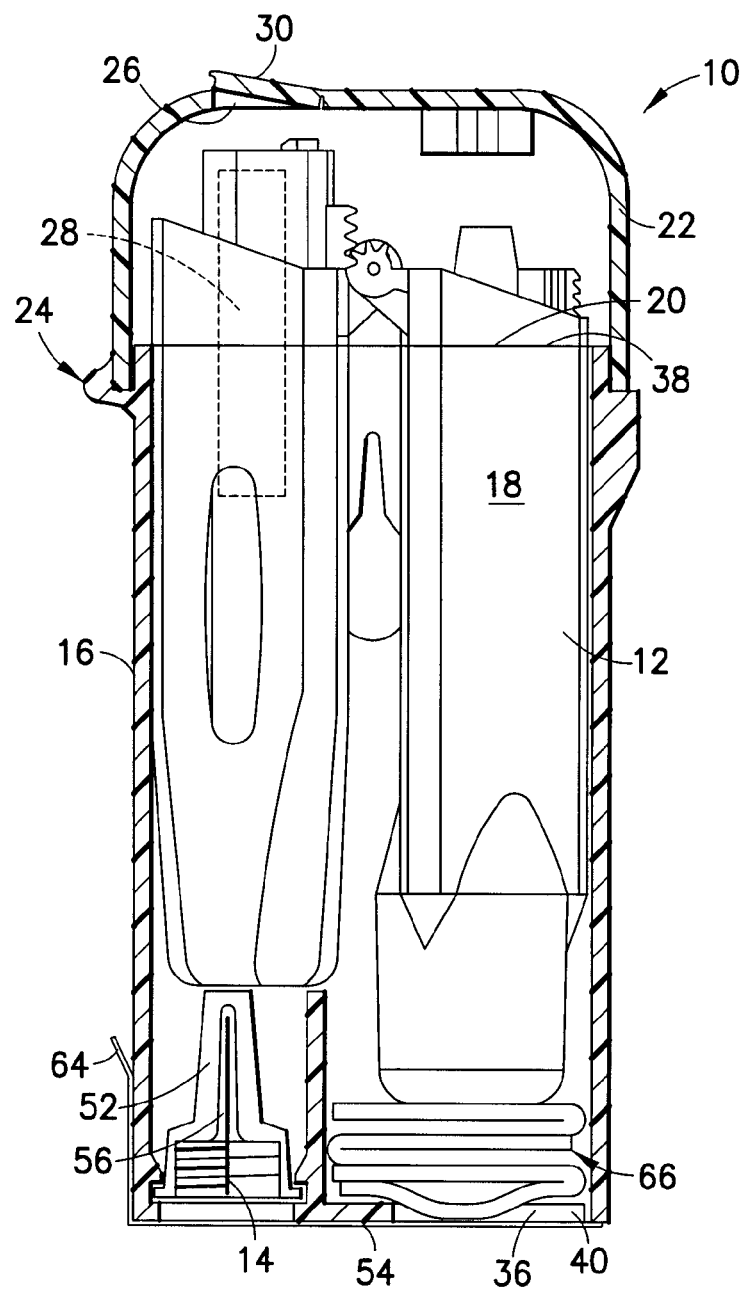
FIG. 2 is a cross-sectional view of the container of FIG. 1.

The container 10 includes a body 16 which defines a compartment 18 formed to accommodate the injection device 12 before use. A first opening 20 is defined in the body 16 through which the injection device 12 may be accessed in a pre-use condition. Preferably, a closure 22 is provided for closing the first opening 20. It is preferred that the closure 22 be attached to the body 16 through an articulating connection 24, which may be a living hinge or a pin hinge. As shown in FIG. 2, in a preferred arrangement, the injection device 12 is wholly enclosed within the container 10, particularly within the compartment 18 with, optionally, a portion being accommodated within the closure 22. The injection device 12 may be disposed in the container 10 in a wholly assembled state ready for use, as shown in FIG. 4, or in a modular or unassembled state, which requires some assembly prior to use, as shown in FIG. 2.

The closure 22 is separable from the body 16 to provide access to the injection device 12, such as by rotation about the articulating connection 24. Thus, the injection device 12 may be packaged, shipped and stored in the container 10 prior to use. With reference to FIG. 2, one or more ports 26 may be formed in the closure 22 to facilitate packaging or assembling of the injection device 12 with the injection device 12 being in the container 10. By way of non-limiting example, and with reference to FIG. 2, the injection device 12 may be provided in an unassembled state in the container 10 with a portion of the injection device 12 being aligned with the port 26. A drug cartridge 28 may be loaded into the injection device 12 through the port 26 with the injection device 12 being in the container 10. This allows for loading of a drug cartridge into an injection device with the injection device remaining packaged. A port closure 30 is preferably provided to normally close the port 26. The port closure 30 may be of any releasably retaining design such as a snap-in tab which is preferably connected or tethered to the closure 22, such as being connected by a living hinge.

It is preferred that once the injection device 12 is removed from the container 10, that the closure 22 be locked to the body 16. As will be appreciated by those skilled in the art, any form of locking arrangement may be utilized. With reference to FIG. 1, and by way of non-limiting example, cooperating tab 32 and recess 34 may be utilized where the tab 32 may become lockingly received in the recess 34, such as through snap engagement.

Figure 3:
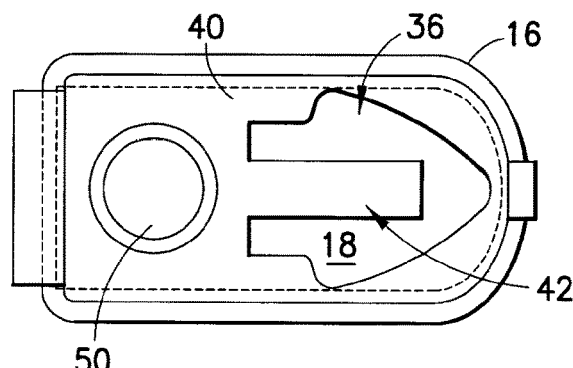
FIG. 3 is a bottom plan view of a container formed in accordance with the subject invention.

Once the injection device 12 has been used (i.e., the injection needle 14 has been used with the injection device 12 to administer an injection), the container 10 may be used to house at least a portion of the injection device 12, with the injection needle 14, in a post-use state. With reference to FIG. 3, a second opening 36 is formed in the body 16 shaped to receive the injection device 12 after use. In a preferred arrangement, the body 16 is generally cup-shaped with the first opening 20 being defined at a first end 38 thereof. It is preferred that the second opening 36 be formed in a second end 40 of the body 16, opposite the first end 38.

Figure 7:
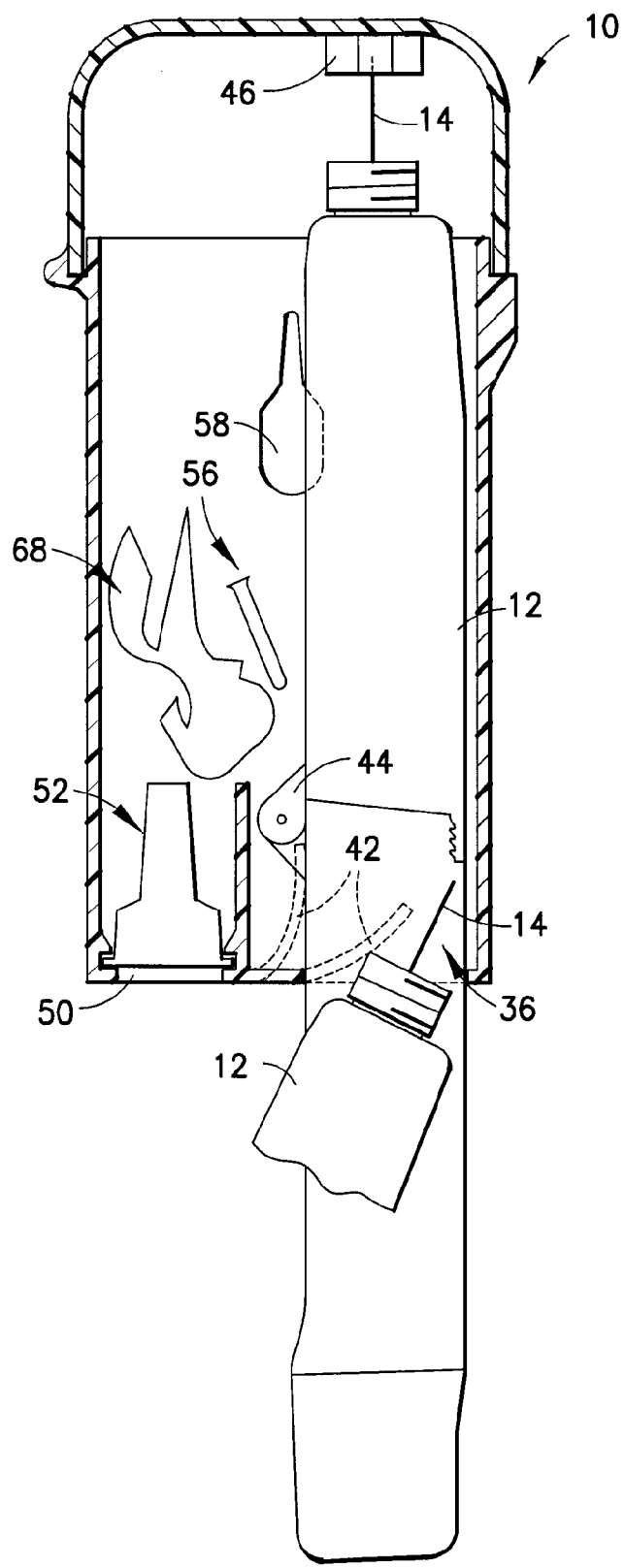
FIG. 7 is a schematic showing a post-use injection device accommodated by a container formed in accordance with the subject invention; and, FIG. 8 is a schematic showing a container formed in accordance with the subject invention being disposed into a sharps container.

The second opening 36 is formed to allow the injection device 12 to cross-sectionally pass therethrough, as shown in FIG. 7. Preferably, a retainer 42 is provided proximate to the second opening 36 to retain the injection device 12 in the container 10 in a post-use condition. As will be appreciated by those skilled in the art, the retainer 42 may be of various configurations. By way of non-limiting example, the retainer 42 may be a flap which engages against a portion of the injection device 12 with sufficient insertion of the injection device 12 into the container 10. The retainer 42 may be resilient to bend upon insertion of the injection device 12 into the second opening 36. Preferably, the injection needle 14 is inserted through the second opening 36 so as to not engage the retainer 42. As shown in FIG. 7, with sufficient insertion of the injection device 12 through the second opening 36, the retainer 42 may interferingly act against an element 44, such as a hinge, provided on the injection device 12, thus, preventing rearward movement of the injection device 12. A rearward tug may be applied to the injection device 12 to ensure that the injection device 12 may not be withdrawn. The retainer 42 may snap engage the element 44, thus providing an audible indication that the injection device 12 has been engaged by the retainer 42. With the injection device 12 being inserted through the second opening 36 with the injection needle 14 leading, the injection needle 14 is housed within the container 10. The retainer 42 prevents withdrawal of the injection device 12, and, thus, limits access to the injection needle 14 in the used state. Furthermore, with the closure 22 being locked to the body 16, the container 10 further limits access to the injection needle 14.

As shown in FIG. 8, the container 10, with the injection device 12 being accommodated therein in a post-use condition, may be disposed of in a sharps container 48. Other appropriate modes of disposal of biohazardous material may be likewise utilized for disposal of the container 10 and the injection device 12 in a post-use state.

The container 10 may be configured to accommodate wholly the injection device 12 in a used state, or, as shown in FIGS. 7 and 8, may be configured to partially accommodate the injection device 12, particularly the portion of the injection device 12 with the injection needle 14.

A pad 46 may be provided in the container 10 positioned to have the injection needle 14 inserted therein in the stored, post-use condition as shown in FIG. 7. The pad 46 may be formed of a resilient or other material pierceable by the injection needle 14. The pad 46 may provide additional retaining force for maintaining the injection device 12 within the container 10.

In a further preferred arrangement, the injection needle 14 is provided in the container 10, prior to use, separately from the injection device 12. A third opening 50 may be provided in the body 16 in which the injection needle 14 is held and made accessible. The injection needle 14 may be retained by a cap 52 fixed to the body 16. A removable seal 54 may be applied across the third opening 50 prior to use. As shown in FIG. 4, with the injection device 12 having been removed from the container 10, the injection device 12 may be inserted into the third opening 50 for mounting of the injection needle 14. The injection needle 14 may be mounted to the injection device 12 using known arrangements, such as a threaded arrangement. Any mounting arrangement may be utilized.

The cap 52 and the removable seal 54 may be configured to create a sterility barrier about the injection needle 14 in a packaged state. In this manner, the injection needle 14 may be sterilized and packaged in the container 10 with sterility of the injection needle 14 being maintained till use. The injection device 12 need not be sterile for use.

Figure 5:
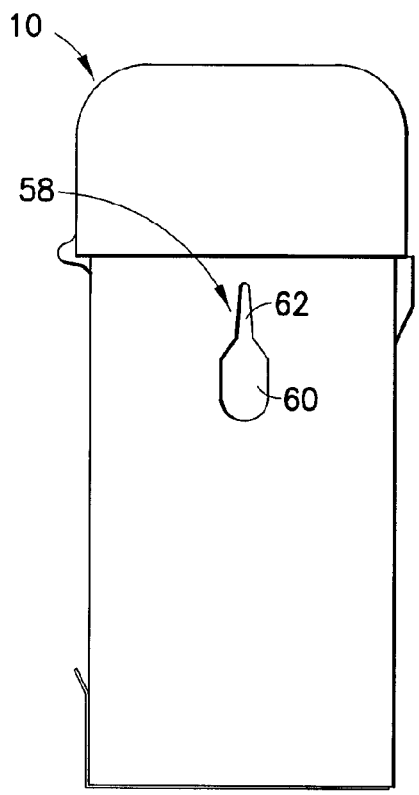
FIG. 5 is a front plan view of a container formed in accordance with the subject invention with an additional opening for removal of a needle shield.
Figure 6:
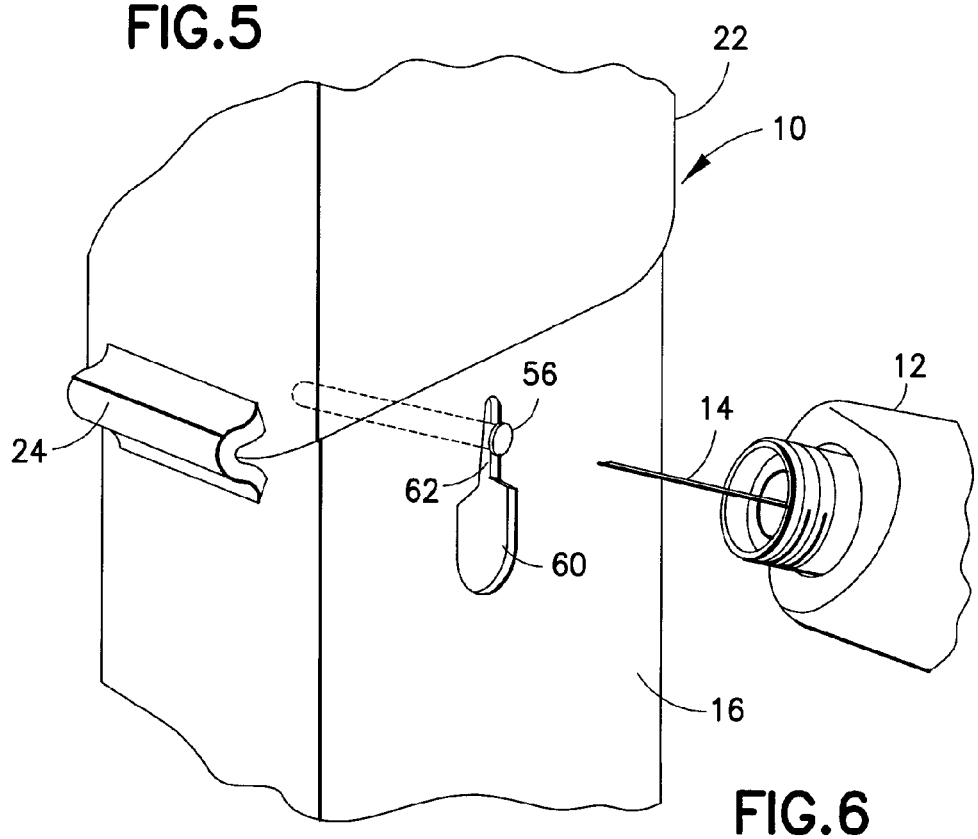
FIG. 6 is a schematic of a needle shield being removed utilizing a container formed in accordance with the subject invention.

To provide additional protection for the injection needle 14, a removable needle shield 56 may be provided which is retained by the cap 52 about the injection needle 14 during storage. The needle shield 56 is mounted onto the injection device 12 along with the injection needle 14. To facilitate removal, the body 16 preferably includes a fourth opening 58, as shown in FIG. 5. The fourth opening 58 includes a first diameter portion 60 and a second diameter portion 62, which is smaller than the first diameter portion 60. The fourth opening 58 is configured such that the needle shield 56 may be inserted into the first diameter portion 60 and wedged into the second diameter portion 62 so as to be gripped by the fourth opening 58. As shown in FIG. 6, with withdrawal of the injection device 12, the needle shield 56 is retained by the fourth opening 58. The used needle shield 56 may remain in the container 10 for disposal therewith (FIG. 7).

With reference to FIG. 2, it is preferred that a removable seal be also provided over the second opening 36. More preferably, it is preferred that the removable seal 54 cover both the second opening 36 and the third opening 50. A pull tab 64 may be provided on the removable seal 54 to facilitate removal thereof.

The container 10 may accommodate additional components, such as swabs 66, which may be betadine and/or alcohol swabs usable to prepare an injection site. Preferably, the swabs 66 are located adjacent to the second opening 36. The retainer 42 may act to retain the swabs 66 within the container 10 and to facilitate individual removal thereof. As shown in FIG. 7, used swabs 68 may be inserted into the container 10 through the second opening 36, prior to the injection device 12 being inserted therein, and/or the fourth opening 58. The used swabs 68 may, thus, be disposed of with the container 10.

What is claimed is:

1. A container for an injection device with an injection needle, the container comprising:
   a body having a compartment formed therein to accommodate said injection device, said body having a usage opening through which the injection device is accessed, said body having a retention opening into which the injection device may be inserted to dispose of said injection device;
   a closure for closing said usage opening; and
   a retention element, wherein said retention element comprises a resilient member that is directly fixed to said body, said retention element contacting said injection device to provide an applied force when at least a portion of said injection device is inserted into said retention opening; wherein a surface defining the usage opening is substantially parallel to a surface defining the retention opening.

2. A container as in claim 1, wherein said body further comprises a needle storage opening,
wherein a part of the injection device is insertable into said needle storage opening for mounting an injection needle contained within said body onto the injection device.

3. A container as in claim 2, wherein said body further comprises
a needle shield removal opening having a first portion with a first diameter and a second portion with a second diameter, said second diameter is smaller than said first diameter, whereby said needle shield removal opening is configured to releasably grip a needle shield provided on the injection needle.

4. A container as in claim 1, wherein said closure is hinged.

5. A container as in claim 4, wherein said hinge is a living hinge.

6. A container as in claim 4, wherein said hinge is a pin hinge.

7. A container as in claim 1, further comprising an access port for loading a medication cartridge into said injection device.

8. A container as in claim 7, wherein said access port is provided with an access port closure.

9. A container as in claim 1, further comprising a removable seal covering said retention opening.

10. A container as in claim 9, wherein said removable seal covers a needle storage opening.

11. A container as in claim 1, wherein said injection device is hinged.

12. A container as in claim 1, further comprising a pad for inserting thereinto a tip of an injection needle.

13. A container for an injection device with an injection needle, the container comprising:
a body having a compartment formed therein to accommodate said injection device, said body having a usage opening through which the injection device is accessed, said body having a retention opening into which the injection device may be inserted to dispose said injection device;
a removable seal covering said retention opening;
a closure for closing said usage opening; and
a retention element, wherein said retention element comprises a resilient member that is fixed inside said body, said retention element contacting said injection device to provide an applied force when at least a portion of said injection device is inserted into said retention opening, said resilient member comprising a bendable flap that covers said retention opening when not engaged, and said removable seal covering said resilient member.

14. A container as in claim 13, further comprising an access port for loading a medication cartridge into said injection device.

15. A container as in claim 14, wherein said access port is provided with an access port closure.

16. A container as in claim 13, wherein said removable seal covers a needle storage opening.

17. A container as in claim 13, wherein said injection device is hinged.

18. A container as in claim 13, further comprising a pad for inserting thereinto a tip of an injection needle.

19. A container as in claim 13, wherein said removable seal is disposed outside of said body.

* * * * *